US009833156B2

(12) United States Patent
Liu et al.

(10) Patent No.: US 9,833,156 B2
(45) Date of Patent: Dec. 5, 2017

(54) HEART RATE DETECTION APPARATUS

(75) Inventors: Shuhai Liu, Beijing (CN); Feng Xu, Beijing (CN); Yanqing Zhang, Beijing (CN)

(73) Assignee: Beijing Choice Electronic Technology Co., Ltd., Beijing (CN)

( * ) Notice: Subject to any disclaimer, the term of this patent is extended or adjusted under 35 U.S.C. 154(b) by 368 days.

(21) Appl. No.: 14/354,729

(22) PCT Filed: Feb. 6, 2012

(86) PCT No.: PCT/CN2012/070887
§ 371 (c)(1),
(2), (4) Date: Apr. 28, 2014

(87) PCT Pub. No.: WO2013/063879
PCT Pub. Date: May 10, 2013

(65) Prior Publication Data
US 2014/0288453 A1    Sep. 25, 2014

(30) Foreign Application Priority Data
Oct. 31, 2011  (CN) .......................... 2011 1 0338093

(51) Int. Cl.
*A61B 5/0245* (2006.01)
*A61B 5/024* (2006.01)
(Continued)

(52) U.S. Cl.
CPC ........ *A61B 5/0245* (2013.01); *A61B 5/02438* (2013.01); *A61B 5/6817* (2013.01);
(Continued)

(58) Field of Classification Search
USPC .......... 381/67, 309, 74, 73.1, 302; 600/483, 600/559, 528, 508, 500, 513
See application file for complete search history.

(56) References Cited

U.S. PATENT DOCUMENTS 5,335,664 A * 8/1994 Nagashima .................... 600/508
6,080,110 A * 6/2000 Thorgersen ............ A61B 5/222
600/322
(Continued)

FOREIGN PATENT DOCUMENTS

CN    101212927 A    7/2008
CN    101873826 A    10/2010
(Continued)

*Primary Examiner* — Davetta W Goins
*Assistant Examiner* — Kuassi Ganmavo
(74) *Attorney, Agent, or Firm* — The Webb Law Firm

(57) ABSTRACT

A heart rate detection apparatus includes a signal acquisition device for acquiring an intra-aural vibration wave signal and converting the intra-aural vibration wave signal into an intra-aural vibration electrical signal; and an arithmetic processing device for processing the intra-aural vibration electrical signal by computing to generate heart rate information. In the prior art, the heart rate detection apparatus cannot accurately and reliably detect the heart rate information due to the weak optical signal detected by a sensor. The heart rate detection apparatus acquires the intra-aural vibration wave signal to obtain the heart rate information, thus enabling the apparatus to accurately and reliably detect heart rate information.

17 Claims, 3 Drawing Sheets

(51) Int. Cl.
*A61B 5/00* (2006.01)
*A61B 5/0456* (2006.01)
*A61B 5/021* (2006.01)
*A61B 7/04* (2006.01)
*A61B 5/0285* (2006.01)

(52) U.S. Cl.
CPC ............ *A61B 5/021* (2013.01); *A61B 5/0285* (2013.01); *A61B 5/02125* (2013.01); *A61B 5/0456* (2013.01); *A61B 5/7221* (2013.01); *A61B 5/7275* (2013.01); *A61B 7/04* (2013.01); *A61B 2562/0204* (2013.01)

(56) References Cited

U.S. PATENT DOCUMENTS

| | | | | |
|---|---|---|---|---|
| 6,454,718 | B1* | 9/2002 | Clift | 600/483 |
| 6,639,538 | B1* | 10/2003 | Sechi et al. | 341/155 |
| 6,647,368 | B2* | 11/2003 | Nemirovski | H04B 1/3877 600/300 |
| 7,137,955 | B2* | 11/2006 | Bartels et al. | 600/528 |
| 7,209,775 | B2* | 4/2007 | Bae | A61B 5/0002 374/E13.003 |
| 2002/0091329 | A1* | 7/2002 | Heikkila et al. | 600/500 |
| 2003/0220584 | A1* | 11/2003 | Honeyager et al. | 600/559 |
| 2003/0233051 | A1* | 12/2003 | Verjus | A61B 5/02438 600/528 |
| 2008/0097228 | A1* | 4/2008 | Aihara | A61B 5/02116 600/490 |
| 2008/0171945 | A1* | 7/2008 | Dotter | A61B 5/024 600/514 |
| 2009/0069645 | A1 | 3/2009 | Nielsen et al. | |
| 2009/0318817 | A1* | 12/2009 | Sakurai | A61B 5/02438 600/490 |
| 2010/0125218 | A1 | 5/2010 | Haartsen et al. | |
| 2010/0324615 | A1* | 12/2010 | Powers | A61B 5/024 607/6 |
| 2014/0107526 | A1* | 4/2014 | Thibaut | A61B 5/4851 600/559 |
| 2014/0323889 | A1* | 10/2014 | Lindman | A61B 5/024 600/508 |

FOREIGN PATENT DOCUMENTS

| | | | |
|---|---|---|---|
| CN | 102215740 A | * 10/2011 | ......... A61B 5/02438 |
| CN | 102327115 A | 1/2012 | |

* cited by examiner

HEART RATE DETECTION APPARATUS

CROSS-REFERENCE TO RELATED APPLICATIONS

This application is the United States national phase of International Application No. PCT/CN2012/070887 filed Feb. 6, 2012, and claims priority to Chinese Patent Application No. 201110338093.5 filed Oct. 31, 2011, the disclosures of which are hereby incorporated in their entirety by reference.

FIELD OF THE INVENTION

The present invention relates to a medical apparatus, and particularly to a heart rate detection apparatus.

BACKGROUND OF THE INVENTION

Generally, heart rate is defined to be the times of heartbeats in one minutes of a person, which is an important medical index reflecting the health condition of the person, and also one important basis for patient care, for directing one to form a good daily routine, and for directing the athletes to train scientifically. The most common apparatus for heart rate detection is stethoscope including many kinds, such as, single head stethoscope, double head stethoscope, triple change stethoscope, stand-type stethoscope, universal stethoscope, and recently appeared electronic stethoscope and the like. In spite of the low price and convenience in use, it's difficult for ordinary persons without professional training to obtain the accurate value of the heart rate using the stethoscope. For example, improper wearing of the stethoscope leads to loose contact between the earplug and the ear canal, such that sounds might leak out, causing a bad auscultation effect; moreover, noise outside might enter to confuse the auscultation effect, such that the value of the heart rate cannot be detected accurately. For another example, if the stethoscope is put in the pocket all the time or not maintained periodically, cotton fiber of the cloth, fiber or dust might block the tube of the stethoscope, which would affect the accuracy of auscultation. Moreover, the accuracy of the stethoscope is so limited that slightly heartbeats or pulse in the irregular heartbeats might be omitted, which also reduces the accuracy.

Recently, with development of photoelectric technology, Photoplethysmograpy (PPG) is widely used in heart rate detection. FIG. 1 is a schematic view of the use of heart rate detection apparatus in the prior art. As shown in FIG. 1, the heart rate detection apparatus 1 is worn on the ear 2, and includes a data processing device, a light source disposed behind the ear, and a sensor located in the auricle and opposite to the light source. After the light signal from the light source transmits through the cartilage of the auricle and is received by the sensor, the date processing device processes the light signal detected by the sensor so as to obtain the heart rate information by computing. The above-mentioned heart rate detection apparatus measures the heart rate by using the light transmission PPG, and the user can wear this heart rate detection apparatus for long time. However, as shapes of auricles of people differ from one another, and the relative position between the heart rate detection apparatus and the auricle cannot keep stable when people move, there occur the conditions that the light signal emitted from the light source cannot transmit through the blood vessel in the auricle or other pulsing region, resulting in weak light signals detected by the sensor, such that the heart rate detection apparatus cannot obtain the heart rate information accurately and reliably.

SUMMARY OF THE INVENTION

The present invention provides a heart rate detection apparatus for detecting the heart rate information accurately and reliably.

To this end, the present invention provides a heart rate detection apparatus, comprising:

a signal acquisition device for acquiring intra-aural vibration wave signal, and converting the intra-aural vibration wave signal into intra-aural vibration electrical signal;

an arithmetic processing device for processing the intra-aural vibration electrical signal by computing to generate the heart rate information.

Furthermore, the signal acquisition device comprises: a signal acquisition unit and a front-end signal processing unit, the signal acquisition unit is used for acquiring the intra-aural vibration wave signal, converting the intra-aural vibration wave signal into the intra-aural vibration electrical signal and outputting the intra-aural vibration electrical signal to the front-end signal processing unit;

the front-end signal processing unit is used for filtering and amplifying the intra-aural vibration electrical signal, and outputting the filtered and amplified intra-aural vibration electrical signal to the arithmetic processing device.

Furthermore, the signal acquisition unit is further used for acquiring vibration wave signal outside the ear, converting the vibration wave signal outside the ear into vibration electrical signal outside the ear, and outputting the vibration electrical signal outside the ear to the front-end signal processing unit;

the front-end signal processing unit is further used for performing compensating and feed-back process to the intra-aural vibration electrical signal according to the vibration electrical signal outside the ear, and outputting the intra-aural vibration electrical signal subjected to the compensating and feed-back process to the arithmetic processing device.

Furthermore, the arithmetic processing device comprises a cache unit, an arithmetic processing unit and a permanent storage unit, the cache unit is used for buffering the intra-aural vibration wave signal;

the arithmetic processing unit is used for obtaining the intra-aural vibration wave signal from the cache unit, processing the intra-aural vibration wave signal by computing to generate the heart rate information, and outputting the heart rate information to the permanent storage unit;

the permanent storage unit is used for storing the heart rate information.

Furthermore, the heart rate detection apparatus further comprises a central control unit and a display unit, the central control unit is used for obtaining the heart rate information from the arithmetic processing unit, and outputting the heart rate information to the display unit;

the display unit is used for displaying the heart rate information.

Furthermore, the heart rate detection apparatus further comprises an alarming unit connected to the central control unit;

the central control unit is further used for generating alarm signal according to the heart rate information, and sending the alarm signal to the alarming unit;

the alarming unit is used for alarming according to the alarm signal.

Furthermore, the heart rate detection apparatus further comprises a communication unit connected to the central control unit and a communication device, the central control unit is further used for outputting the heart rate information to the communication unit;

the communication unit is used for outputting the heart rate information to the communication device.

Furthermore, the heart rate detection apparatus further comprises an input unit connected to the central control unit, the input unit is used for sending operation instruction to the central control unit;

the central control unit is further used for carrying out the operations instructed by the operation instruction according to the operation instruction.

Furthermore, the central control unit is further used for obtaining standard heart rate information through the communication unit, and adjusting the heart rate information according to the standard heart rate information.

Furthermore, the heart rate information comprises value of heart rate, status value of the heart rate, and/or status value of heartbeat.

Furthermore, the signal acquisition unit includes one or more acoustical-electrical transducers, and the probe direction of each acoustical-electrical transducer is adjustable in a predetermined angle range.

Furthermore, the arithmetic processing unit is specifically used for computing the value of heart rate according to the number of pulses in the intra-aural vibration electrical signal, and the status value of the heart rate and/or the status value of heartbeat according to the intensity of the intra-aural vibration electrical signal.

Furthermore, the status value of the heart rate or the status value of heartbeat is at a level among several predetermined levels.

Furthermore, the alarm signal comprises sound signal, optical signal, vibration signal or arbitrary combination thereof.

Furthermore, On and Off, volume up and down and/or strength of vibration of the alarming unit are controlled by the central control unit.

Furthermore, the heart rate detection apparatus adjusts and learns the heart rate information on the basis of comparison with the standard heart rate information.

Furthermore, the input unit controls On and Off of operation mode of the heart rate detection apparatus, the display unit, the alarming unit, and the communication unit.

Furthermore, a user can control the heart rate detection apparatus by detection control software in the communication device.

Furthermore, the heart rate detection apparatus is an earmuff-type heart rate detection apparatus, a supra aural-type heart rate detection apparatus, an earplug-type heart rate detection apparatus, or an in-the-canal-type heart rate detection apparatus.

The above technical solutions have the following advantages: the present invention provides a heart rate detection apparatus comprising a signal acquisition device and an arithmetic processing device. The signal acquisition device is used for acquiring intra-aural vibration wave signal and converting the intra-aural vibration wave signal into intra-aural vibration electrical signal. The arithmetic processing device is used for processing the electrical signal of vibration in the ear by computing to generate the heart rate information. Unlike the prior art solutions wherein the heart rate information is obtained by acquiring the related signal at the auricle, the heart rate detection apparatus provided by the present invention obtains the heart rate information by acquiring the intra-aural vibration wave signal. As a result, using the heart rate detection apparatus according to the present invention to detect heart rate can avoid the problem that the heart rate cannot be detected accurately and reliably as the light signal detected by the sensor is too weak in the prior art. In other words, the heart rate detection apparatus according to the present invention can detect the heart rate accurately and reliably.

DETAILED DESCRIPTION OF THE PREFERRED EMBODIMENTS

The heart rate detection apparatus according to the present invention will be described in detail with reference to the accompanied drawings for better understanding of those skilled in the art.

Figure 1:
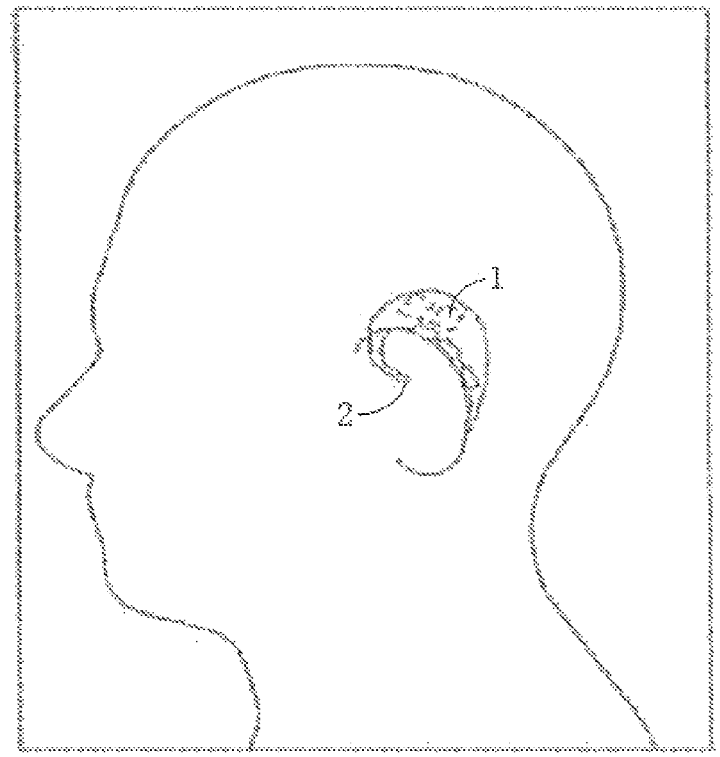
FIG. 1 is a schematic view of the use of the heart rate detection apparatus in prior art.
Figure 2:
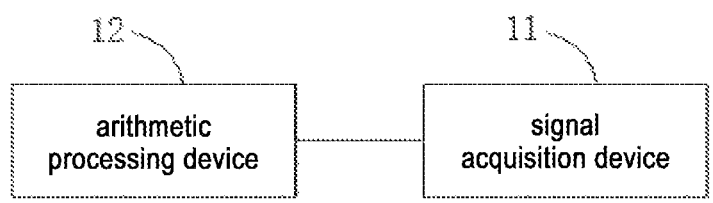
FIG. 2 is a configuration diagram of the heart rate detection apparatus according to the first embodiment of the present invention.

FIG. 2 is a configuration diagram of the heart rate detection apparatus according to the first embodiment of the present invention. As shown in FIG. 2, the heart rate detection apparatus includes a signal acquisition device 11 and an arithmetic processing device 12.

The signal acquisition device 11 is used for acquiring intra-aural vibration wave signal, and converting the vibration wave signal into intra-aural vibration electrical signal.

Inside of the ear is part with maximum blood vessels in all of the human organs, and blood vessels inside the ear lead to the brain where blood vessels are more intensive. There is tympanic membrane located in the tympanic cavity with lots of blood vessels and arterial blood inside the ear. Blood flows one-way under the effect of auricular systole and dilatation, during which the vibration wave signal caused by blood flowing through the inside of the ear is stronger, and the vibration wave signal caused by flood inside the ear is conducted into the ear canal by the tympanic membrane, such that vibration wave signal conducted by the tympanic membrane can reflect the status of heart rate truly and reliably. Furthermore, vibration wave signal caused by blood inside the ear can be also conducted into the ear canal by bones and/or tissues which are the cartilage inside the ear and bones and/or tissues which are not the cartilage inside the ear. In each embodiments of the present invention, intra-aural vibration wave signal mainly includes vibration wave signal caused by blood flowing inside the ear and conducted into the ear canal by the tympanic membrane, and vibration wave signal conducted into the ear canal by bones and/or tissues which are the cartilage inside the ear and bones and/or by tissues which are not the cartilage inside the ear. The signal acquisition device 11 acquires the above-mentioned intra-aural vibration wave signal to detect the heart rate information. Besides, the signal acquisition device 11 converts the intra-aural vibration electrical signal into digitized intra-aural vibration electrical signal, such that the arithmetic processing device 12 can process the intra-aural vibration electrical signal. Alternatively, the arithmetic processing device 12 can convert the intra-aural vibration electrical signal into digitized intra-aural vibration electrical signal and then carry out subsequent processing to the intra-aural vibration electrical signal.

The arithmetic processing device 12 is used for computing and processing the intra-aural vibration electrical signal to generate the heart rate information. In the present embodiment, the heart rate information may comprise value of heart rate, status value of the heart rate, and/or status value of heartbeat. Correspondingly, the processing procedures of the arithmetic processing device 12 computing and processing the intra-aural vibration electrical signal specifically comprises: the arithmetic processing device 12 computes the value of heart rate according to the pulses in the intra-aural vibration electrical signal, the status value of the heart rate, and/or status value of heartbeat according to the intensity of the intra-aural vibration electrical signal.

The heart rate detection apparatus provided by the present embodiment comprises a signal acquisition device and an arithmetic processing device. The signal acquisition device is used for acquiring intra-aural vibration wave signal and converting the intra-aural vibration wave signal into intra-aural vibration electrical signal. The arithmetic processing device is used for computing and processing the electrical signal of vibration in the ear to generate the heart rate information. The heart rate detection apparatus of the present embodiment obtains the heart rate information by acquiring the intra-aural vibration wave signal, thus the heart rate can be detected accurately and reliably, and the problem that the heart rate information cannot be detected accurately and reliably as the light signal detected by the sensor is too weak in the prior art can be avoided.

Figure 3:
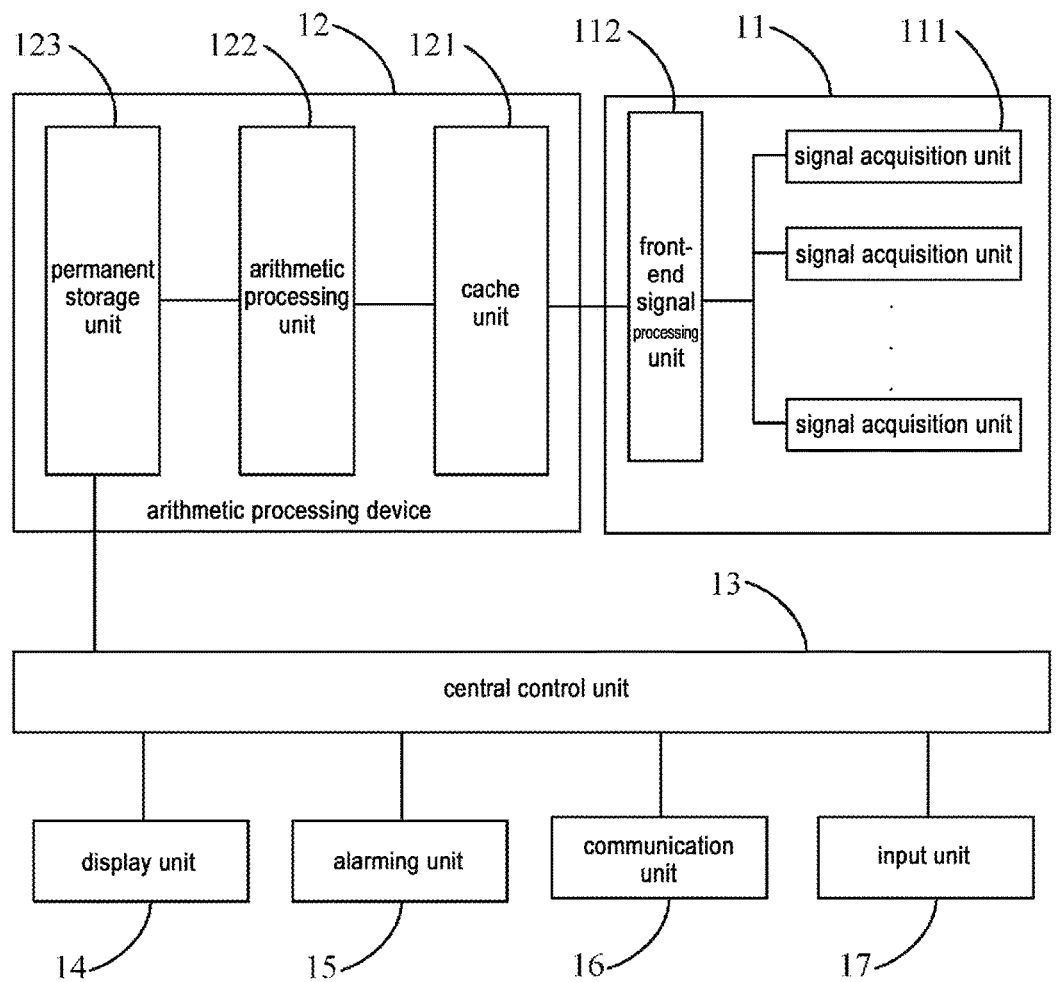
FIG. 3 is a configuration diagram of the heart rate detection apparatus according to the second embodiment of the present invention.

FIG. 3 is a configuration diagram of the heart rate detection apparatus according to the second embodiment of the present invention. As shown in FIG. 3, the heart rate detection of the present embodiment is further configured on the basis of the first embodiment. The second embodiment is disclosed here as an improvement to the first embodiment, and the improvement made to the first embodiment is an optional configuration provided or installed in the heart rate detection apparatus of the first embodiment. The second embodiment can be also configured in the heart rate detection apparatus of the prior art to form new embodiment.

In the second embodiment, the signal acquisition device comprises a signal acquisition unit 111 and a front-end signal processing unit 112.

In the present embodiment and the first embodiment, the signal acquisition unit 111 is used for acquiring the intra-aural vibration wave signal, converting the intra-aural vibration wave signal into intra-aural vibration electrical signal and outputting the intra-aural vibration electrical signal to the front-end signal processing unit 112. There could be one or more signal acquisition units 111, and in the present embodiment, description will be made by referring to more than one signal acquisition units. The signal acquisition unit 111 of the present embodiment may be an acoustical-electrical transducer which is a sensor that can convert sound vibration wave into electrical signal. The probe direction of each acoustical-electrical transducer is adjustable in a predetermined angle range, thus in practical use, the probe direction of the acoustical-electrical transducer can be adjusted to align with the tympanic membrane, such that the vibration wave conducted by the tympanic membrane can be acquired thoroughly, precisely, efficiently and effectively when the heart rate detection apparatus is worn on the ear. Specifically, the signal acquisition unit 111 converts the intra-aural vibration electrical signal into digitized intra-aural vibration electrical signal. The front-end signal processing unit 112 is used for filtering and amplifying the intra-aural vibration electrical signal, and outputting the filtered and amplified intra-aural vibration electrical signal to the arithmetic processing device 12. Furthermore, the signal acquisition unit 111 is further used for acquiring vibration wave signal outside the ear, converting the vibration wave signal outside the ear into vibration electrical signal outside the ear, and output the vibration electrical signal outside the ear to the front-end signal processing unit 112, wherein, the vibration wave signal outside the ear comprises vibration wave signal produced by vessel in the auricle, signal of any object not to be detected outside the ear and all the signals that may interference the detection of the present invention; in this case, the front-end signal processing unit 112 is further used for performing compensating and feed-back process to the intra-aural vibration electrical signal according to the vibration electrical signal outside the ear, and outputting the intra-aural vibration electrical signal after the compensating and feedback process to the arithmetic processing device 12. More than one signal acquisition units 111 can be disposed on the surface of a hemisphere or an approximate hemisphere, and may be disposed on the spherical surface out of the hemisphere as desired, such that some of a signal acquisition units 111 are used for acquiring signals conducted by the tympanic membrane, and other signal acquisition units 111 face towards the external ear canal to acquire vibration wave signals outside the ear. At the same time, the front-end signal processing unit 112 can perform compensating and feed-back processing to the intra-aural vibration electrical signal according to the vibration electrical signal outside the ear to improve the detection precision. Wherein, the spherical surface on which the signal acquisition units 111 are disposed may be perfect spherical surface, or irregular spherical surface tilting directly towards the direction of the tympanic membrane. Furthermore, the spherical surface on which the signal acquisition units 111 are disposed may be other forms of spherical surface, such as any spherical surface designed according to ergonomic, made of different materials, with different shape and size, thus the user can freely chose the spherical surface he/she feels comfortable, i.e. selecting different signal acquisition unit 111. Besides, signal acquisition units 111 with different accuracy can be provided in the signal acquisition device 11 to meet requirements of different users or occasions.

Furthermore, in the present embodiment and the first embodiment, the arithmetic processing device 12 specifically comprises: a cache unit 121, an arithmetic processing unit 122 and a permanent storage unit 123. The cache unit 121 is used for buffering the intra-aural vibration wave signal; the arithmetic processing unit 122 is used for obtaining the intra-aural vibration signal from the cache unit 121, processing the intra-aural vibration wave signal to generate the heart rate information, and outputting the heart rate information to the permanent storage unit 123; the permanent storage unit 123 is used for storing the heart rate information. The heart rate information comprises value of heart rate, status value of the heart rate, and/or status value of heartbeat. Correspondingly, the specific procedure that the arithmetic processing unit 122 processes the intra-aural vibration electrical signal comprises: the arithmetic processing unit 122 computes the value of heart rate according to the pulses in the intra-aural vibration electrical signal, the status value of the heart rate, and/or status value of heartbeat according to the intensity of the intra-aural vibration electrical signal. Wherein, the value of heart rate, status value of the heart rate, and/or status value of heartbeat may be classified into several predetermined levels. For example, the status value of heartbeat may be classified into three levels including healthy, sub-healthy and abnormal to provide basis and reference for diagnosing, monitoring and treating symptom such as arrhythmia; status value of the heart rate may correspond to five heart healthy levels ranging from A to E, wherein, level A stands for tachycardia, level E stands for bradycardia, and other levels have like meanings between level A and level E. Furthermore, the status value of the heartbeat may be re-classified and re-defined according to other standards, and the status value of the heart may be re-classified and re-defined into different levels according to other cardiac health indicators or pulsation indicators, not limited to the kinds and definitions proposed herein. Alternatively, the converting of intra-aural vibration electrical signal into digitized intra-aural vibration electrical signal may be carried out by the cache unit 121 in the arithmetic processing device 12.

Furthermore, in the present embodiment and the first embodiment, the heart rate detection apparatus may further comprises: a central control unit 13 and a display unit 14. The central control unit 13 is used for obtaining the heart rate information from the arithmetic processing unit 12, and outputting the heart rate information to the display unit 14. Specifically, the central control unit 13 may obtain the heart rate information from the permanent storage unit 123 of the arithmetic processing device 12. The display unit 14 is used for displaying the heart rate information. The display unit 14 may be Liquid Crystal Display, Light Emitting Diode (LED) display or Organic Light-Emitting Diode (OLED) display. Functional circuit controlling on or off of the backlight may be provided in the display unit 14; the central control unit 13 may sent backlight-on instruction to the functional circuit in the display unit 14 to turn on the backlight according to the backlight-on instruction, or the central control unit 13 may sent backlight-off instruction to the functional circuit in the display unit 14 to turn off the backlight according to the backlight-on instruction.

Furthermore, in the present embodiment or the first embodiment, the heart rate detection apparatus may further comprise an alarming unit 15 connected with the central controlling unit 13. The central control unit 13 is further used for generating alarm signal according to the heart rate information, and sending the alarm signal to the alarming unit 15. For example, a safe range of the heart rate information can be predetermined, and then if the central control unit 13 determines that the heart rate information is out of the safe range, the alarm signal will be generated. Wherein, the alarm signal may comprise sound signal, light signal, vibration signal or arbitrary combination thereof. The alarming unit 15 is used for alarming according to the alarm signal. Furthermore, the central control unit 13 may send alarm-on instruction to control turning-on of the alarming unit 15, alarm-off instruction to control turning-off of the alarming unit 15, alarm-volume instruction to control the volume up or down, or vibration-strength instruction to control the vibration strength. Wherein, the alarm-volume instruction may control muting of the alarming unit 15. In conclusion, on and off, volume up and down and/or strength of vibration of the alarming unit 15 are controlled by the central control unit 13.

Furthermore, in the present embodiment or the first embodiment, the heart rate detection apparatus may further comprise a communication unit 16 connected with the central control unit 13 and a communication device. The central control unit 13 is further used for outputting the heart rate information to the communication unit 16; the communication unit 16 is used for outputting the heart rate information to the communication device. In the present embodiment, the communication unit 16 may be a wired communication unit, a wireless communication unit or the combination thereof; the communication device may include mobile communication device such as mobile phone, MP3, MP4 or PDA. The central control unit 13 transmits the heart rate information to the communication device through the communication unit 16, then the communication device displays the heart rate information, uploads the heart rate information to the Internet, sends the heart rate information to the doctor's e-mail box, performs data analysis of the heart rate information and other operation.

Furthermore, in the present embodiment or the first embodiment, the heart rate detection apparatus has the functions of self-learning and self-correcting implemented by the central control unit 13, the software carrying out these functions is written in for example the permanent storage unit 123. The heart rate detection apparatus can correct and learn the heart rate information on the basis of comparison with the standard heart rate information. Specifically, by the self-learning and self-correcting functions, the user can obtain the standard heart rate information at the hospital and the like when his/her heart rate is stable, and then the user may use the heart rate detection apparatus of the present invention to detect the heart rate information and store it into the permanent storage unit 123. At the same time, via the communication unit 16, a precise heart rate testing instrument is connected with the central control unit 13 which may be further used for obtaining the standard heart rate information, according to which the heart rate information is corrected (for example, the heart rate information may be corrected by filtering values too high or too low).

Furthermore, in the present embodiment or the first embodiment, the heart rate detection apparatus further comprises an input unit 17 connected with the central control unit 13. The input unit 17 is used for sending operation instruction to the central control unit 13; the central control unit 13 is further used for carrying out the operation instructed by the operation instruction according to the operation instruction. The operation instruction sent by the input unit 17 may includes switching instruction that controls on and off of the heart rate detection apparatus, backlight-on instruction or backlight-off instruction that controls the backlight of the display unit, alarm-on instruction or alarm-off instruction that controls the alarming function of the alarming unit, alarm-volume instruction that controls the volume up or down of the alarming unit 15, or vibration-strength instruction that controls the vibration strength of the alarming unit 15, or operation mode switching instruction that controls the operation mode of the communication unit 16, wherein, the operation mode switching instruction can control the communication unit 16 to switch between wireless communication mode and wire communication mode. The input unit 17 may be provided with a control panel, and by operating the control panel the user may send the above-mentioned operation instructions to the central control unit 13, wherein, the control panel may include touch screen or panel with several buttons or knobs. Otherwise, the input unit 17 may further be provided with a speech control circuit, by which the user may send the above-mentioned operation instructions to the central control unit 13 in a manner of speech control.

In particular, in each embodiment of the present invention, when the communication device communicatively (wirelessly or by wires) connected to the communication unit 16 has detection control software, the heart rate detection apparatus of the present embodiment may not include the input unit 17. At the same time, the user may control the heart rate detection apparatus by the detection control software in the communication device. Specifically, the user can send the operation instructions to the central control unit 13 via the detection control software in the communication device. The above-mentioned detection control software can be readily implemented by those skilled in the art or programmer without creative work, for example, application software for various applications running in the recently fashionable IPHONE.

Figure 4:
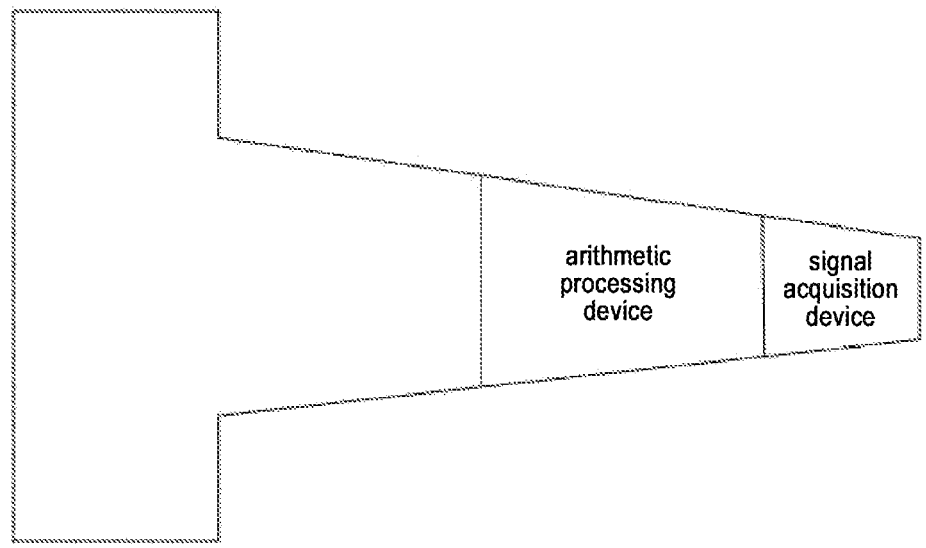
FIG. 4 is a schematic diagram of the use of the heart rate detection apparatus according to the present invention.
Figure 5:
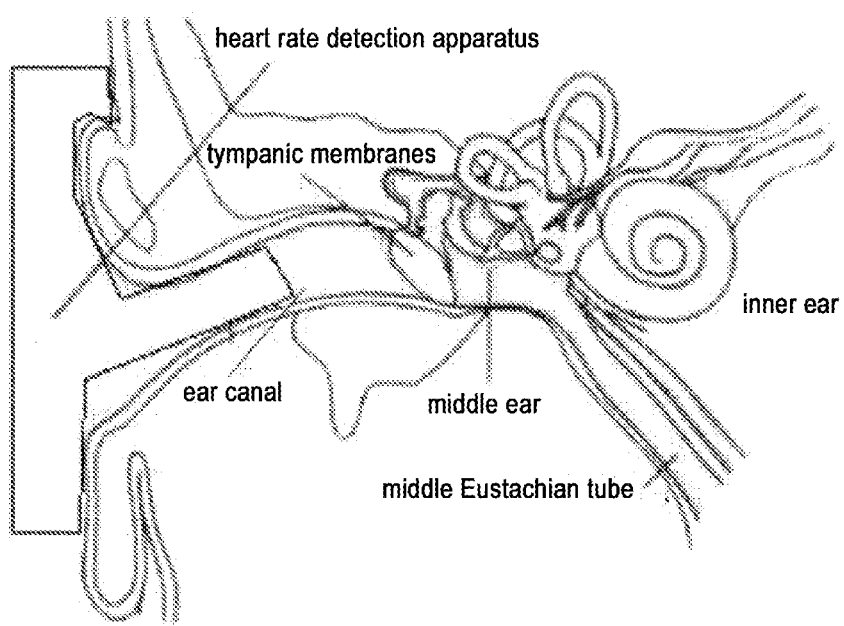
FIG. 5 is a configuration diagram of the heart rate detection apparatus shown in FIG. 4.

In each embodiment of the present invention, the heart rate detection apparatus is worn on the ear in use, such that the heart rate detection apparatus may be an earmuff-type heart rate detection apparatus, a supra aural-type heart rate detection apparatus, an earplug-type heart rate detection apparatus, or an in-the-canal-type heart rate detection apparatus. Wherein, the appearance of the earmuff-type heart rate detection apparatus may be the same as that of the earmuff-type earphone, and the appearance of the supra aural-type heart rate detection apparatus may be the same as that of the supra aural-type earphone, the appearance of the earplug-type heart rate detection apparatus may be the same as that of the earplug-type earphone, and the appearance of the in-the-canal-type heart rate detection apparatus may be the same as that of the in-the-canal-type earphone. The following description refers to the in-the-canal-type heart rate detection apparatus. FIG. 4 is a schematic structural diagram of heart rate detection apparatus provided by the present invention in use, and FIG. 5 is a configuration diagram of the heart rate detection apparatus shown in FIG. 4. As shown in FIG. 4 and FIG. 5, the heart rate detection apparatus is an in-the-canal-type heart rate detection apparatus. The signal acquisition device is disposed at the most front-end end of the heart rate detection apparatus, the arithmetic processing device is disposed at the central portion of the heart rate detection apparatus, and other components of the heart rate detection apparatus are disposed at other positions. When the heart rate detection apparatus is worn on the ear, the signal processing device is in the canal, and aligning with the tympanic membrane, such that the detection of the heart rate information can be carried out.

The heart rate detection apparatus provided by the present embodiment comprises a signal acquisition device and an arithmetic processing device. The signal acquisition device is used for acquiring intra-aural vibration wave signal and converting the intra-aural vibration wave signal into intra-aural vibration electrical signal. The arithmetic processing device is used for computing and processing the electrical signal of vibration in the ear to generate the heart rate information. The heart rate detection apparatus provided by the present embodiment obtains the heart rate information by acquiring the intra-aural vibration wave signal, thus avoiding the problem in the prior art that the heart rate cannot be detected accurately and reliably as the light signal detected by the sensor is too weak. Thus the heart rate detection apparatus provided by the present invention can detect the heart rate accurately and reliably.

The heart rate detection apparatus of the present embodiment obtains the heart rate information by acquiring the intra-aural vibration wave, thus avoiding the influence of "stethoscope effect" and "bone conduction phenomenon" on the detection process of the heart rate information and the accuracy of the detected heart rate information. The heart rate detection apparatus may be an earmuff-type heart rate detection apparatus, a supra aural-type heart rate detection apparatus, an earplug-type heart rate detection apparatus, or an in-the-canal-type heart rate detection apparatus, such that the user may wear the heart rate detection apparatus in the canal or at the edge of the ear continuously without feeling uncomfortable. The heart rate detection apparatus has low cost and simple structure, and is easy to repair with low maintenance cost when it malfunctions. The heart rate detection apparatus is easy to operate without requirements of professional medical knowledge during the operating process.

Although the present invention has been disclosed with reference to the above preferred embodiments, the present invention is not limited thereto. Various modifications and improvements to the present invention can be made by ordinary skilled persons in the art without departing from the concept and substance of the present invention, and these modifications and improvements fall within the protection scope of the present invention.

What is claimed is:
1. A heart rate detection apparatus, comprising:
a signal acquisition device for acquiring an intra-aural vibration wave signal and converting the intra-aural vibration wave signal into an intra-aural vibration electrical signal, wherein the intra-aural vibration wave signal comprises vibration wave signals caused by blood flowing inside an ear and conducted into an ear canal of the ear by a tympanic membrane and vibration wave signals conducted into the ear canal by bones and/or tissues that are cartilage inside the ear and by bones and/or tissues that are not cartilage inside the ear; and
an arithmetic processing device for processing the intra-aural vibration electrical signal by computing to generate heart rate information,
wherein the signal acquisition device comprises a signal acquisition unit and a front-end signal processing unit,
wherein the signal acquisition unit is used for
acquiring the intra-aural vibration wave signal,
converting the intra-aural vibration wave signal into the intra-aural vibration electrical signal,
outputting the intra-aural vibration electrical signal to the front-end signal processing unit,
acquiring a vibration wave signal outside the ear, which comprises a vibration wave signal produced by a vessel in an auricle of the ear,
converting the vibration wave signal outside the ear into a vibration electrical signal outside the ear, and
outputting the vibration electrical signal outside the ear to the front-end signal processing unit, and
wherein the front-end signal processing unit is used for
filtering and amplifying the intra-aural vibration electrical signal,
outputting the filtered and amplified intra-aural vibration electrical signal to the arithmetic processing device,
performing a compensating and feedback process to the intra-aural vibration electrical signal based on the vibration electrical signal outside the ear, and
outputting the intra-aural vibration electrical signal subjected to the compensating and feedback process to the arithmetic processing device.

2. The heart rate detection apparatus of claim 1, wherein the arithmetic processing device comprises a cache unit, an arithmetic processing unit and a permanent storage unit;

the cache unit is used for buffering the intra-aural vibration wave signal;
the arithmetic processing unit is used for obtaining the intra-aural vibration wave signal from the cache unit, processing the intra-aural vibration wave signal by computing to generate the heart rate information, and outputting the heart rate information to the permanent storage unit; and
the permanent storage unit is used for storing the heart rate information.

3. The heart rate detection apparatus of claim 2, further comprising a central control unit and a display unit, wherein, the central control unit is used for obtaining the heart rate information from the arithmetic processing unit, and outputting the heart rate information to the display unit; and
the display unit is used for displaying the heart rate information.

4. The heart rate detection apparatus of claim 3, further comprising an alarming unit connected to the central control unit; wherein, the central control unit is further used for generating an alarm signal according to the heart rate information, and sending the alarm signal to the alarming unit; and
the alarming unit is used for alarming according to the alarm signal.

5. The heart rate detection apparatus of claim 4, further comprising a communication unit connected to the central control unit and a communication device, wherein, the central control unit is further used for outputting the heart rate information to the communication unit; and
the communication unit is used for outputting the heart rate information to the communication device.

6. The heart rate detection apparatus of claim 5, further comprising an input unit connected to the central control unit, wherein, the input unit is used for sending an operation instruction to the central control unit; and
the central control unit is further used for carrying out an operation instructed by the operation instruction according to the operation instruction.

7. The heart rate detection apparatus of claim 6, wherein the input control unit controls On and Off of operation mode of the heart rate detection apparatus, the display unit, the alarming unit, and the communication unit.

8. The heart rate detection apparatus of claim 5, wherein the central control unit is further used for obtaining standard heart rate information through the communication unit, and adjusting the heart rate information according to the standard heart rate information.

9. The heart rate detection apparatus of claim 5, wherein a user can control the heart rate detection apparatus by detection control software in the communication device.

10. The heart rate detection apparatus of claim 4, wherein the alarm signal comprises a sound signal, an optical signal, a vibration signal or combinations thereof.

11. The heart rate detection apparatus of claim 10, wherein On and Off, volume up and volume down, and/or strength of vibration of the alarming unit are controlled by the central control unit.

12. The heart rate detection apparatus of claim 1, wherein, the heart rate information comprises value of heart rate, status value of the heart rate, and/or status value of heartbeat.

13. The heart rate detection apparatus of claim 1, wherein the signal acquisition unit includes one or more acoustical-electrical transducers, and a probe direction of each acoustical-electrical transducer is adjustable in a predetermined angle range.

14. The heart rate detection apparatus of claim 1, wherein the arithmetic processing unit is used for computing the value of heart rate according to the number of pulses in the intra-aural vibration electrical signal, and computing a status value of the heart rate and/or a status value of heartbeat according to the intensity of the intra-aural vibration electrical signal.

15. The heart rate detection apparatus of claim 14, wherein the status value of the heart rate or the status value of heartbeat is at a level among several predetermined levels.

16. The heart rate detection apparatus of claim 1, wherein the heart rate detection apparatus adjusts and learns the heart rate information on the basis of a comparison with standard heart rate information.

17. The heart rate detection apparatus of claim 1, wherein the heart rate detection apparatus is an earmuff-type heart rate detection apparatus, a supra aural-type heart rate detection apparatus, an earplug-type heart rate detection apparatus, or an in-the-canal-type heart rate detection apparatus.

* * * * *